United States Patent
Elliott

(10) Patent No.: US 8,043,321 B2
(45) Date of Patent: Oct. 25, 2011

(54) EMBOLIC COIL

(75) Inventor: Christopher J. Elliott, Hopkinton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1544 days.

(21) Appl. No.: 10/626,246

(22) Filed: Jul. 24, 2003

(65) Prior Publication Data
US 2005/0021074 A1     Jan. 27, 2005

(51) Int. Cl.
*A61M 29/00*     (2006.01)
(52) U.S. Cl. .................................... 606/200
(58) Field of Classification Search ............... 606/200, 606/1, 108, 191, 151, 213, 194–198; D24/143; 128/831, 843; 623/1.11, 1.12, 11.1
See application file for complete search history.

(56) References Cited

U.S. PATENT DOCUMENTS

| | | | | |
|---|---|---|---|---|
| 5,304,194 A * | 4/1994 | Chee et al. | ......... | 606/191 |
| 5,382,259 A * | 1/1995 | Phelps et al. | ......... | 606/151 |
| 5,382,260 A * | 1/1995 | Dormandy et al. | ......... | 606/151 |
| 5,522,822 A * | 6/1996 | Phelps et al. | ......... | 606/151 |
| 5,549,624 A * | 8/1996 | Mirigian et al. | ......... | 606/191 |
| 5,582,619 A * | 12/1996 | Ken | ......... | 606/191 |
| 5,658,308 A * | 8/1997 | Snyder | ......... | 606/191 |
| 5,690,667 A * | 11/1997 | Gia | ......... | 606/191 |
| 5,749,894 A * | 5/1998 | Engelson | ......... | 606/213 |
| 5,797,953 A * | 8/1998 | Tekulve | ......... | 606/200 |
| 5,843,118 A * | 12/1998 | Sepetka et al. | ......... | 623/1.15 |
| D411,618 S * | 6/1999 | Mariant et al. | ......... | D24/143 |
| 5,919,187 A * | 7/1999 | Guglielmi et al. | ......... | 606/32 |
| 5,944,714 A * | 8/1999 | Guglielmi et al. | ......... | 606/32 |
| 5,980,514 A * | 11/1999 | Kupiecki et al. | ......... | 606/32 |
| 6,024,765 A * | 2/2000 | Wallace et al. | ......... | 606/191 |
| 6,033,423 A * | 3/2000 | Ken et al. | ......... | 606/200 |
| 6,063,111 A * | 5/2000 | Hieshima et al. | ......... | 623/1.22 |
| 6,117,157 A * | 9/2000 | Tekulve | ......... | 606/200 |
| 6,143,007 A * | 11/2000 | Mariant et al. | ......... | 606/151 |
| 6,165,178 A * | 12/2000 | Bashiri et al. | ......... | 606/108 |
| 6,171,326 B1 * | 1/2001 | Ferrera et al. | ......... | 606/191 |
| 6,221,066 B1 * | 4/2001 | Ferrera et al. | ......... | 606/1 |
| 6,280,457 B1 * | 8/2001 | Wallace et al. | ......... | 606/200 |
| 6,287,318 B1 * | 9/2001 | Villar et al. | ......... | 606/191 |
| 6,383,204 B1 | 5/2002 | Ferrera et al. | | |
| 2002/0010481 A1 * | 1/2002 | Jayaraman | ......... | 606/151 |
| 2004/0002733 A1 * | 1/2004 | Teoh | ......... | 606/200 |
| 2004/0098028 A1 * | 5/2004 | Martinez | ......... | 606/200 |

FOREIGN PATENT DOCUMENTS

| | | |
|---|---|---|
| EP | 0 820 726 | 1/1998 |
| EP | 0 865 773 | 9/1998 |
| WO | 02/096302 | 12/2002 |

\* cited by examiner

*Primary Examiner* — Elizabeth Houston
(74) *Attorney, Agent, or Firm* — Vista IP Law Group LLP

(57) ABSTRACT

An embolic coil comprises an elongated core element formed of a shape memory material treated to define a memorized secondary coil shape and an elongated outer element wound around the elongated core element to define a primary coil shape of the embolic coil. A method of forming an embolic coil, comprises the steps of imparting a memorized shape to a core element formed of a shape memory material, wherein the memorized shape defines a secondary coil of the embolic coil and straightening the core element in combination with the steps of winding an elongated outer element around the straightened core element to form a primary coil of the embolic coil and releasing the straightened core element when the device has been positioned at a deployment location to form the secondary coil of the embolic coil.

14 Claims, 5 Drawing Sheets

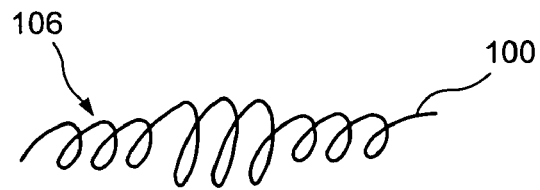
F I G. 5a
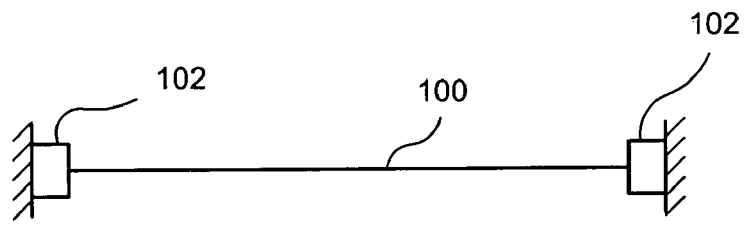
F I G. 5b
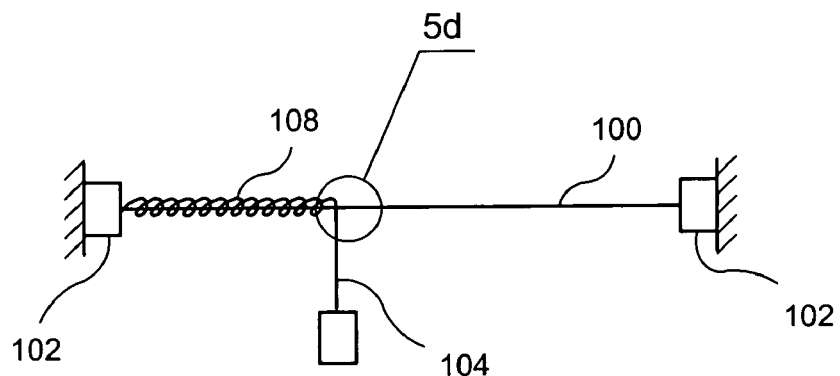
F I G. 5c
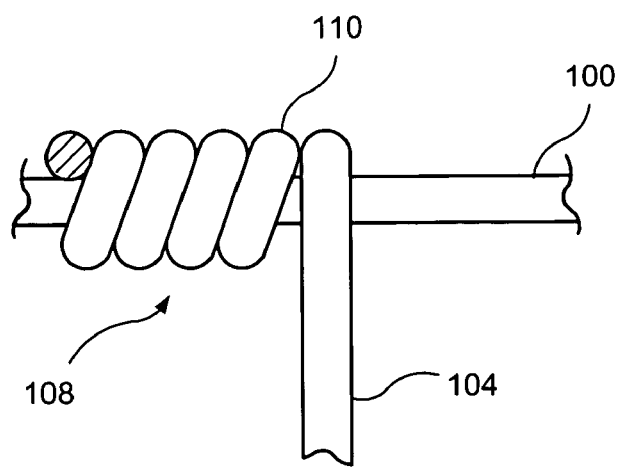
F I G. 5d

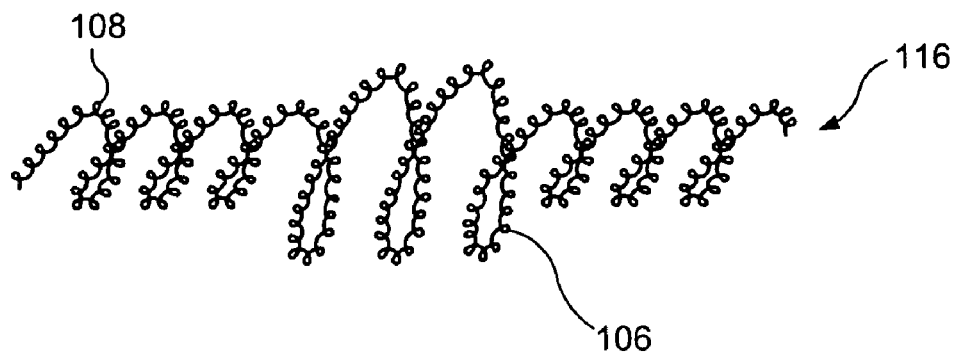
F I G. 6
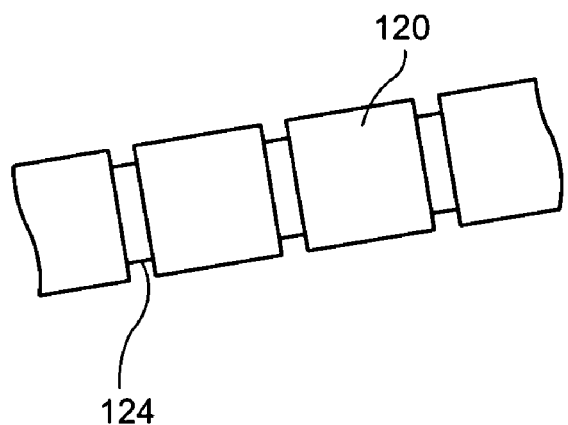
F I G. 7
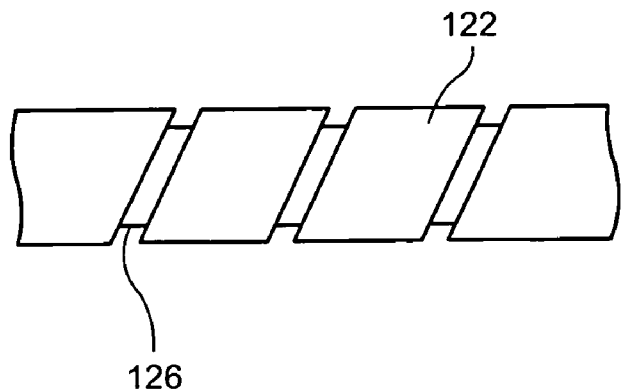
F I G. 8

EMBOLIC COIL

BACKGROUND OF THE INVENTION

Many clinical situations require the reduction or complete stoppage of blood flow to some region of the patient's body. Embolic coils are one example of devices that may be used to stop undesired blood flow in situations, for example, requiring treatment of aneurysms, arteriovenous malformations, traumatic fistulae and tumor embolization. These conditions require that the blood flow through a portion of a blood vessel be stopped, for example by introducing an artificial device into the vessel to slow the flow to allow the natural clotting process form a more complete blockage.

Embolic coils are made from a bio-compatible material, such as platinum, to minimize problems associated with tissue irritation and rejection. These coils are often shaped as complex three dimensional curves that fill in portions of a blood vessel's lumen and slow blood flow therethrough. Often, polymeric fibers are added to the metallic coils to enhance the coil's thrombogenicity (i.e., its ability to cause the formation of clots).

In the treatment for an aneurysm, an embolic coil is inserted in the affected blood vessel using a catheter, and is placed within the bulging, weakened section of the blood vessel. When in place, the coil expands to its operational size and shape, and slows down the flow of blood through the weakened section. Over time, a clot forms around the embolic coil, and blood flow through the weakened section is completely blocked. Thus, failure of this weakened section is less likely and the resulting hemorrhage may be prevented.

Typical embolic coils are formed using two major steps: 1) a wire of platinum or other bio-compatible material is wound into a spring, forming what is commonly referred to as a primary coil; and 2) the primary coil is in turn wound around a mandrel having a more complex shape and is subject to high heat to yield a secondary coil. The secondary coil thus is a coiled wire of complex-shape. Subsequently, polymeric fibers may be added to the embolic coil, usually between the rings of the primary coil.

SUMMARY OF THE INVENTION

In one aspect, the present invention is directed to an embolic coil comprising an elongated core element formed of a shape memory material treated to define a memorized secondary coil shape and an elongated outer element wound around the elongated core element to define a primary coil shape of the embolic coil. The invention also includes a method of forming an embolic coil which comprises the steps of setting a shape memory core element to a shape defining a secondary coil shape of the embolic coil, straightening the core element, winding an elongated outer element around the straightened core element to form a primary coil of the embolic coil, and releasing the straightened core element to form the secondary coil of the embolic coil.

In another aspect, the invention is directed to a method of forming an embolic coil, comprising the steps of imparting a memorized shape to a core element formed of a shape memory material, wherein the memorized shape defines a secondary coil of the embolic coil and straightening the core element in combination with the steps of winding an elongated outer element around the straightened core element to form a primary coil of the embolic coil and releasing the straightened core element when the device has been positioned at a deployment location to form the secondary coil of the embolic coil.

BRIEF DESCRIPTION OF THE DREWINGS

FIG. 5 is a diagram showing a shape memory primary coil / mandrel according to an embodiment of the invention;

FIG. 6 is a diagram showing winding of a platinum wire on a shape memory mandrel according to an embodiment of the present invention;

FIG. 7 is a diagram showing a Nitinol winding core with fiber retainers according to an embodiment of the invention;

FIG. 8 is a diagram showing a Nitinol winding core with fiber retainers according to a second embodiment of the invention.

DETAILED DESCRIPTION

Figure 1A:
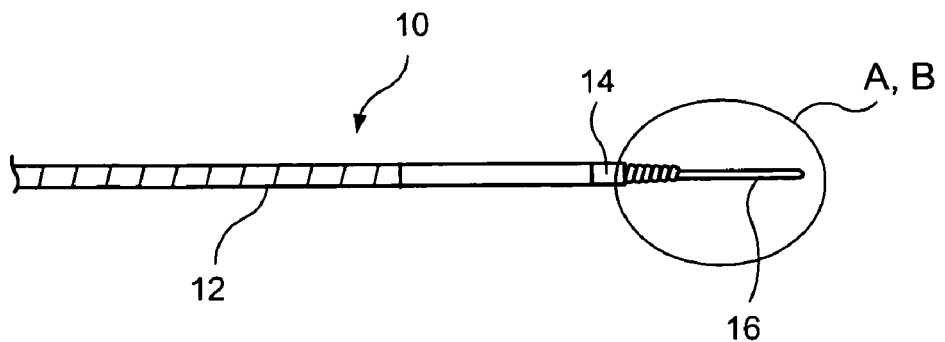
FIG. 1A is a diagram showing an exemplary embolic coil according to the present invention.

The present invention may be further understood with reference to the following description and the appended drawings, wherein like elements are referred to with the same reference numerals. The present invention is related to medical devices used to block the flow of blood through a blood vessel such as, for example, embolic coils. Although the following description relates primarily to embolic coils having a primary and secondary coil winding, the invention is also applicable to other devices that include in their construction complex coil shapes.

Traditionally, aneurysms have been very difficult to diagnose, since the patients are generally asymptomatic until the aneurysm bursts. At that point, most of the damage has already taken place, and available medical therapies have been limited. Even in cases where the aneurysm has been identified prior to bursting, the medical options have been limited, because the aneurysm is often in locations that are difficult to reach by surgery, and repairing the damaged blood vessel may be impossible. Recent advances in visualization methods, however, have made the early identification of aneurysms and similar problems more common. Once the aneurysm has been located, it may be treated by blocking the supply of blood to the weakened area even if surgery to repair the blood vessel is not practical.

Figure 1B:
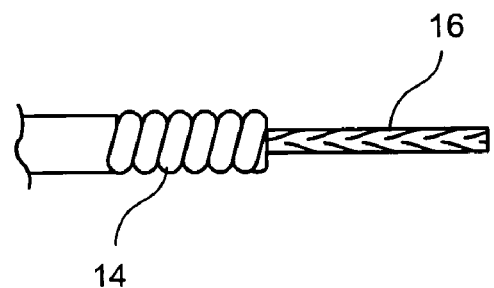
FIG. 1B shows a detailed view of the coil of FIG. 1A in a pre-deployment configuration.
Figure 1C:
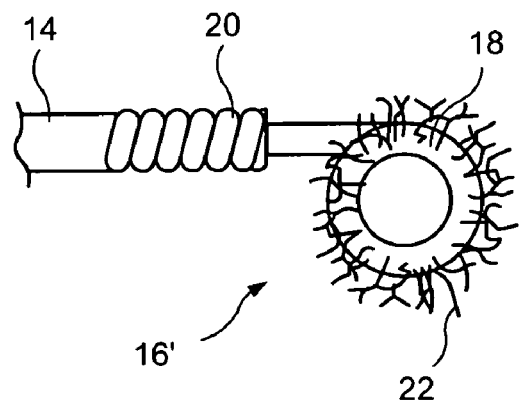
FIG. 1C shows a detailed view of the coil of FIG. 1A in a post-deployment configuration.

FIG. 1 is a diagram showing an exemplary embolic coil to which embodiments of the present invention are applicable, and an exemplary delivery system for the coil. The coil delivery system 10 may be used, for example, for arterial and venous embolization via a catheter. A delivery wire 12 is inserted in a catheter (not shown) which has been introduced into the patient's vascular system. A distal portion 14 of the wire 12 may include radiopaque markers to facilitate positioning of a coil 16 at a desired location within the blood vessel (e.g., adjacent to the weakened or damaged portion thereof). All or part of the wire 12 may be flexible, so that it may follow the curvature of the catheter leading to the region of the vascular system to be treated.

The coil 16 is shown in detail in FIG. 1A in a folded configuration, suitable for insertion through a catheter into the vascular system with minimal discomfort to the patient. For example, in the folded configuration, the coil 16 may have the shape of a bundle of straight parallel wires. Once the coil 16 has reached the desired position within the vascular system, it may be deployed to its operative configuration and released from the wire 12 so that it will remain in position at the proper location. The deployed coil 16' shown in detail in FIG. 1B comprises several elements that confer to it the desired properties. A primary coil 20 forms the basic element of the embolic coil 16, and is generally formed by a tightly wound spiral of platinum wire. Those skilled in the art will understand that other suitably bio-compatible materials may be used instead of platinum so long as they possess appropriate mechanical properties. The primary coil 20 is, in turn, wound into another coiled shape to form a secondary coil 18 and to give an overall shape to the embolic coil 16. The secondary coil 18 may be a simple coil having a pitch and width that are substantially constant along its length. In the alternative, the pitch and width of the secondary coil 18 may vary in shape and dimension along its length, to fit into and to maintain its position in a specified space within the vascular system.

Optionally, an embolic coil 16' may also include a plurality of fibers 22 that extend from its surface. The fibers 22 increase the surface area of the coil 16' that is in contact with the flow of blood, and thus make the coil 16' more efficient at slowing the flow of blood therethrough. This enhances the formation of clots that will further preclude blood flow through the region where the coil 16' is deployed. For example, the fibers 22 may be formed from strands of polymeric fibers such as Dacron or Nylon, or other durable materials that do not cause reactions with tissues of the human body. The fibers 22 may be held in place, for example, by friction between the loops of the primary coil 20, such that a certain amount of pressure between the loops is necessary to securely retain the fibers 22 therebetween.

Figure 2:
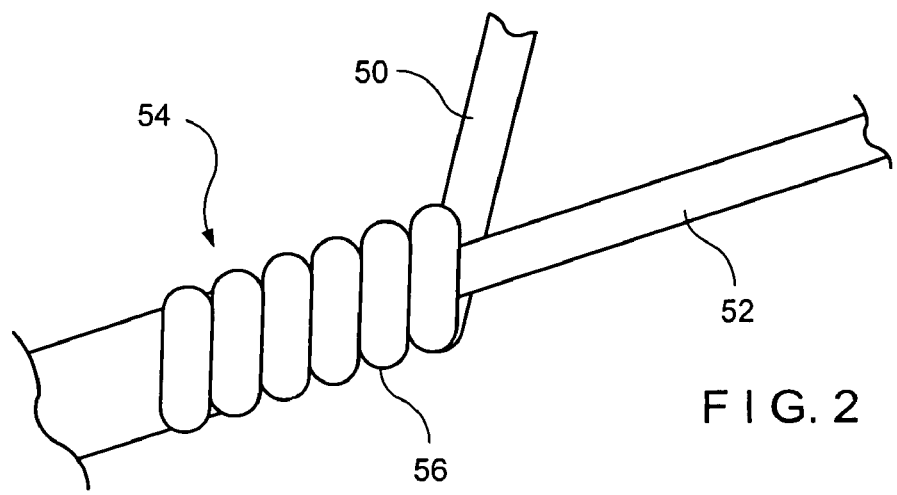
FIG. 2 is a diagram showing a primary coil winding for an embolic coil according to an embodiment of the invention.
Figure 3:
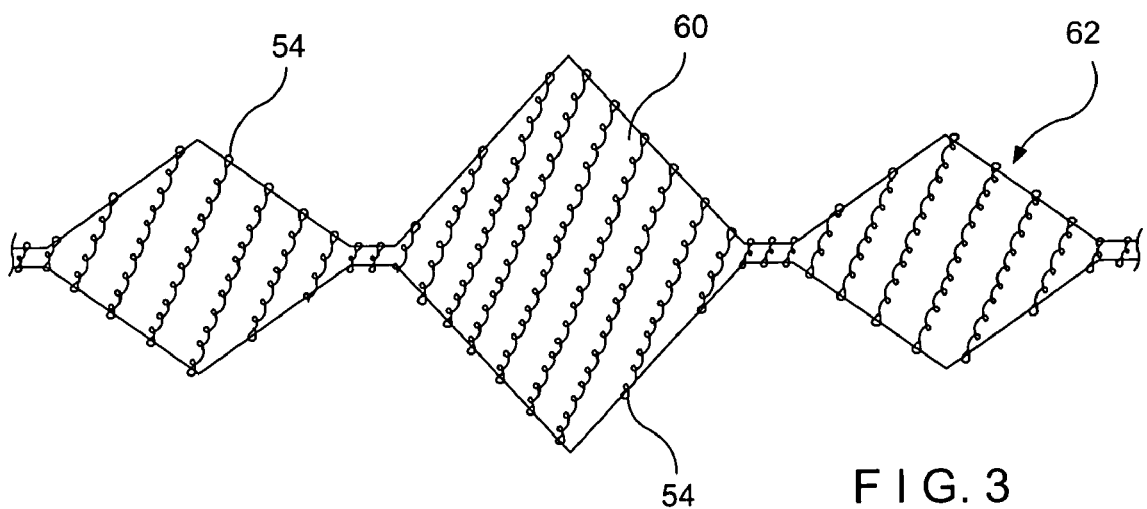
FIG. 3 is a diagram showing a secondary coil winding for a conventional embolic coil.

FIGS. 2 and 3 show a conventional process for constructing the primary and secondary coils of an embolic coil. In this process, the coil is formed by first winding a platinum wire 50 on a primary winding mandrel 52. The resulting primary coil 54 has a wire-like elongated appearance, and can be treated as a flexible wire in subsequent operations. The process of winding the platinum wire 50 on the primary mandrel 52 performs cold work on the platinum wire 50, which as a result is plastically deformed into the coiled shape of the primary coil 54. The amount of cold work performed on the wire 50 determines how well the loops 56 retain their shape and remain tightly in contact with one another. The amount of cold work thus influences the ability of the primary coil 54 to retain the fibers 22 (shown in FIG. 1) that may be part of the embolic coil.

Figures 4A, 4B:
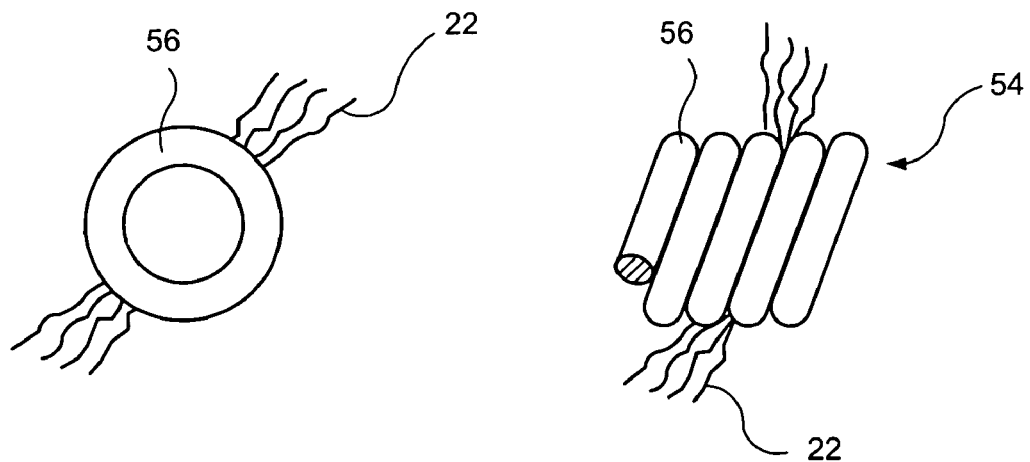
FIG. 4 is a diagram showing attachment of polymeric fibers to the primary coil according to an embodiment of the invention.

A second step in constructing an embolic coil is shown in FIG. 4. In this step, the primary coil 54 is in turn wound around a secondary coil mandrel 60 to form a secondary coil 62. The secondary mandrel 60 may have a cylindrical shape resulting in a simple cylindrical coil shape for the secondary coil 62, or may have a more complex shape, as shown, to generate the secondary coil 62 that conforms to a desired size and shape. For example, the secondary coil 62 may have a variable coil diameter and/or a variable pitch. Exemplary shapes of the secondary coil include helices, vortices, flat spirals, complex spirals, 3D complex shapes etc., as required by any specific clinical application. The specific details of the size and shape of the secondary coil 62 thus can be selected to fit the requirements of the medical procedure for which the embolic coil is to be used.

After the primary coil 54 has been wound around the secondary coil mandrel 60, heat is applied to the assembly to set and maintain the secondary coil 62 in the shape of the secondary winding mandrel 60. For example, a temperature of 1000° F. to 1200° F. may be necessary to ensure that the secondary coil 62 retains its shape once it has been removed from the secondary winding mandrel 60. The shape of the secondary coil 62 is an important parameter which determines the anchorability of the device in the patient's vascular system. The various shapes that can be given to the secondary winding ensure that the embolic coil remains in position within the blood vessel, and is not dislodged by the movement of blood therethrough or by movements of the patient. For example, an embolic coil may be designed so that, after introduction into a portion of a blood vessel weakened by an aneurysm, the embolic coil expands upon deployment to a helical, spiral or other shape that ensures the embolic coil will remain within the weakened portion of the blood vessel.

FIG. 4 shows an exemplary embodiment of fibers 22 being attached to the primary coil 54 of an embolic coil. As indicated above, the fibers 22 may be polymeric fibers or may be made of other flexible materials, for example, Nitinol. The fibers 22 are added to the platinum primary coil 54 to impart greater thrombogenicity to the overall embolic coil, and to increase its ability to stop the undesired flow of blood therethrough. The fibers 22 are generally inserted between the loops 56 of the primary coil 54, and are held in place by virtue of the cold work imparted to the platinum wire during the primary coil winding process. In an exemplary embodiment, the insertion of the fibers 22 in the loops 56 is carried out after the heat treatment used to set and maintain the shape of the secondary coil 62.

However, other processes may be better suited to forming embolic coils having enhanced shape retention and fiber retention properties. Specifically, the retention of the fibers 22 between the loops 56 of the primary coil 54 is a function of the amount of cold work that has been performed and that continues to affect the platinum wire 50. In other words, the fibers 22 remain in place more securely when a large amount of cold work is performed that is not later removed. On the other hand, the overall anchorability of the embolic coil within a specified portion of the vascular system depends on retaining the specified shape of the embolic cord. This shape is best retained when the secondary winding of primary coil 54 on secondary mandrel 60 is subject to a high temperature for an extended time period. A high temperature treatment results in an embolic coil that maintains its complex three dimensional shape more accurately.

The heating process used to set the shape of the secondary coil, however, has an annealing effect on the platinum wire, which reverses the effect of the cold work performed when winding the primary coil. On a molecular level, cold working a metal wire refers to causing plastic deformations to the metal which introduce strain in the crystal structure of the material. The strain results in hardening of the metal and changes the shape of the metal. Annealing refers to heating and then cooling a material to remove internal stresses and to make the material less brittle, so that the material becomes more flexible after annealing. In the case of the platinum wire wound onto the primary coil, annealing causes the coil loops 56 (shown in FIG. 4) to be kept together less tightly, so that the fibers 22 are not retained with as much force as before the annealing. Construction of the embolic coil using this procedure therefore involves a compromise between the shape retention properties and the fiber retention properties of the finished coil, since the high temperature treatment used for better shape retention also anneals the cold work from primary winding, leading to reduced fiber retention.

According to further embodiments of the present invention, embolic coils are provided that exhibit both improved shape retention and improved fiber retention properties. The exemplary coils according to the invention are capable of retaining the fibers used to increase the device's thrombogenicity, while at the same time retaining their shape which makes them capable of remaining in position within the vascular system against forces applied by a strong flow of blood and other factors. According to embodiments of the invention, the exemplary embolic coils are not treated with high heat to set and maintain the secondary coil shape. Instead, a memory shape material is used to impart to the assembly the secondary coil shape.

As shown in FIG. 5, a core wire 100 made of a shape memory material, such as Nitinol, is formed in the shape of a secondary coil 106 (FIG. 5a). As indicated above, the secondary coil 106 may have a variety of shapes, such as a spiral, an helix, a two or three dimensional complex shape, etc. As will be apparent to those of skill in the art, conventional methods may be used to fix the shape of the shape memory alloy wire to the desired configuration. For example, plastic deformation of the wire when above a critical temperature of the material (the austenite finishing temperature Af), followed by cooling of the material may be carried out, so that the material will "remember" the shape imparted to it, as would be understood by those of skill in the art. Once the desired shape for the wire 100 has been memorized, the wire 100 retains the final general shape of the embolic coil, as shown in FIG. 5a. As shown in FIG. 5b, the wire 100 is then stretched between restraints 102 and is used as the winding mandrel to form the primary coil. In this step, the wire 100 may also be cooled below its critical temperature to facilitate the stretching operation. For example, the critical temperature may below the operational temperature of the device, i.e. room temperature.

In one exemplary embodiment shown in FIG. 5c, a wire such as a platinum wire 104 is wound around the straightened and stretched shape memory wire 100, when the latter is below its critical temperature. As the wire 104 is wound, it assumes the shape of a primary coil 108, and at the same time it is subjected to cold work which plastically deforms it into the desired shape. Loops 110 are formed and are kept tight against one another by internal strain resulting from the cold work. As described above, the primary coil 108 may, for example, have a simple, cylindrical shape when the wire 104 is wound around a constant diameter mandrel such as the shape memory wire 100.

Once the primary coil winding of the wire 104 over the mandrel/shape memory wire 100 has been completed, the restraints 102 may be released to free the shape memory wire 100 to resume its previously memorized shape. If the stretching and primary coil winding are carried out at a temperature below the critical temperature of the shape memory wire 100, a temperature increase may be necessary to restore the wire 100 to its memorized shape. Otherwise, simply releasing the restraints 102 frees the shape memory wire 100 to resume the shape of secondary coil 106. The resulting embolic coil 116 is shown in FIG. 6, where the shape of primary coil 108 is superimposed on the outline of the larger, more complex shape of the secondary coil 106. According to embodiments of the invention, no heat treatment or only minimal heat treatment is necessary to set and maintain the secondary coil shape. Thus the cold work imparted to the platinum wire during primary winding is not adversely affected by subsequent annealing. According to the present exemplary embodiment, the embolic coil 116 thus comprises a Nitinol core wire disposed within the lumen of the platinum primary coil.

As would be understood by those of skill in the art, the shape memory properties of alloys such as Nitinol may be understood in terms of the phase transformations the alloy undergoes under various conditions. Shape memory refers to the ability of a structure to revert to an originally memorized shape after plastic deformation by heating it above a critical temperature. This plastic deformation may significant—to the extent that it would be permanent in a structure formed of non-shape memory material. These Nitinol alloys can exist in two conditions, depending on the temperature and the strains applied thereto. At temperatures above the critical temperature the alloy is in an austenite phase and, below that temperature, it remains in a martensite phase. In addition, austenitic portions of the alloy may become martensitic when a strain is applied thereto.

Heating the alloy above the critical temperature in a desired shape causes the alloy to "memorize" that shape. As the temperature is lowered below the critical temperature, the alloy changes phase and becomes malleable in the martensite phase. If a strain is then applied to the alloy element to plastically deform it, the alloy remains martensitic, but now has a different shape due to the deformation. As this deformation is plastic, this new shape is maintained even after the strain has been removed. If the alloy element is later heated above the critical temperature, a thermoelastic martensitic transformation takes place and the element returns to its original memorized shape, regaining the strength and rigidity of the austenitic phase.

Those skilled in the art will also understand that alloys such as Nitinol also exhibit superelasticity effects. That is, when a strain is applied to the alloy element in the austenitic phase, the element deforms this deformation may generate large areas of strain-induced martensite material even if there is no temperature change. These areas occur primarily at points of where the strain is highest and may result in deformations that would be unrecoverable in normal materials. However, at that temperature martensite is not the stable phase of the alloy, and as soon as the strain has been removed the alloy returns to an austenitic state and reverts to its original shape. Superelasticity thus refers to the ability of the alloy, while in the austenitic state, to deform under strain to a very large degree, without having this deformation become permanent.

Superelasticity effects are useful in devices designed for use within the human body. For example, a superelastic embolic coil according to embodiments of the invention can easily be restrained into a small, streamlined configuration for insertion into the body, for example through a catheter. Then, when the embolic coil has been positioned at a desired location within the vascular system, restraints may be removed allowing the coil to deploy to an expanded operational configuration. Superelasticity also allows the coil to bend greatly due to, e.g., strains imparted during normal activities of the patient, without losing its ability to return to its operational state after the strains have been removed.

According to embodiments of the present invention, the embolic coil 116 thus includes a shape memory core element, for example a wire made of Nitinol, which gives to the assembly the secondary coil shape 106. Around the shape memory core element is wound an elongated outer element, such as another wire made, for example, of platinum, which forms the primary coil 108 of the device. Fibers may be added to the primary coil 108 to increase the thrombogenicity of the coil, as discussed above. Since little or no annealing takes place according to embodiments of the invention, the cold work applied during primary winding is not reduced, and thus fiber retention between the loops 110 of primary coil 108 is maximized. Embodiments of the present invention thus exhibit both enhanced fiber retention due to the high cold work applied to the primary coil and enhanced shape retention which translates to easy anchorability in position due to the shape memory alloy core.

Additional enhancements may be made to the embolic coil according to the present invention, to improve the device's fiber retention properties. For example, as shown in FIG. 7, the shape memory core wire 120 may comprise cylindrical grooves 124 that are used as anchors for fibers. Grooves 124 channel the fiber bundles around core wire 120, so that they are held in place by the core wire 120. In this manner the primary coil 108 is freed from that function. Channeling the fiber bundles via grooves 124 promotes cohesion of the fibers, and reduced the loss of fibers during use of the embolic coil. In a different embodiment shown in FIG. 8, a shape memory core wire 122 may comprise spiral grooves 126, which also help anchor fibers such as the fibers 22 shown in FIG. 4. In these embodiments, the amount of cold work imparted to the primary coil 108 has less effect on how well the fibers 22 are retained, and fewer restrictions are imposed on the shape and properties of the primary coil 108.

Figure 9:
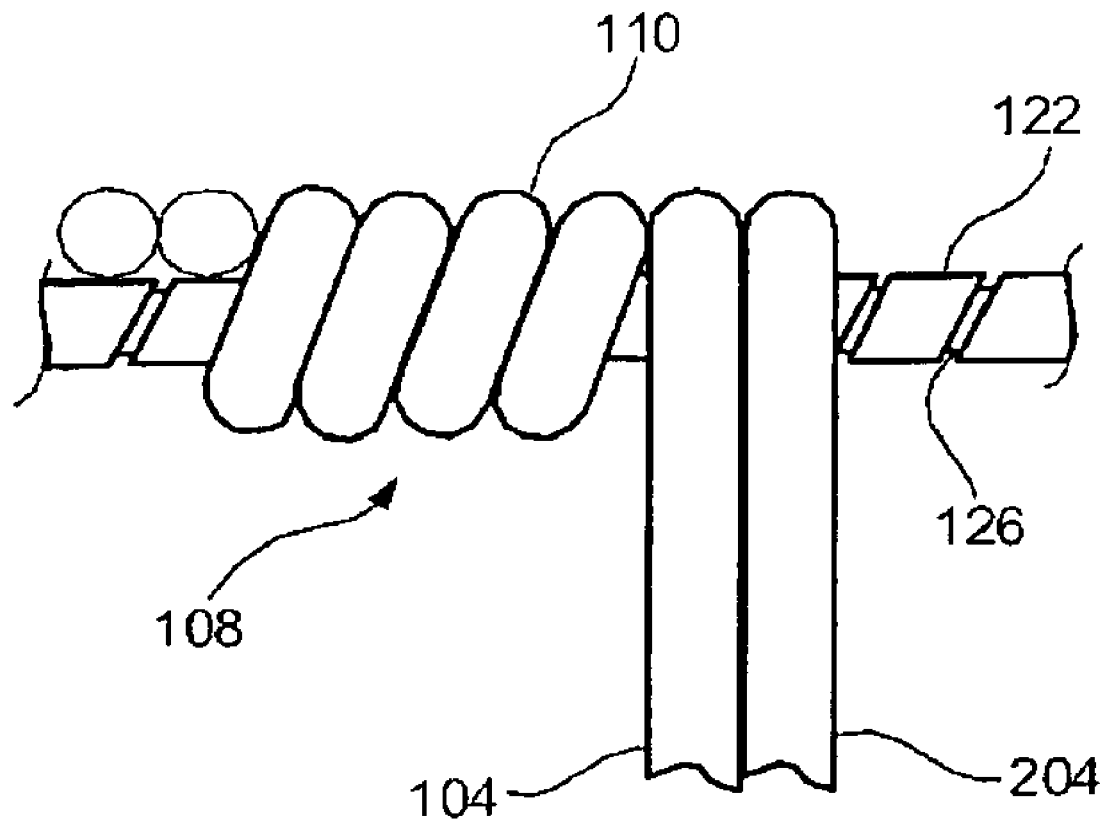
FIG. 9 is a diagram showing a shape memory core wire with fiber retainers and co-winding of a platinum wire and a second wire made of a shape memory material according to an embodiment of the invention.

In a different embodiment, the platinum wire forming the primary coil 108 may be co-wound with a second wire made of a shape memory material. A heat setting process may be used to set and maintain the shape of primary coil 108, by relying on the properties of the shape memory material wire. More complex designs of the primary coil 108 may thus be obtained without reducing the fiber retention capability of the device. FIG. 9 shows this embodiment. Platinum wire 104 of primary coil 108 is co-wound with the second wire 204 that is made of a shape memory material. Both wires are wound around shape memory core wire 122. Shape memory core wire 122 may comprise spiral groves 126, which help anchor fibers such as the fibers 22 shown in FIG. 4. Because spiral groves 126 may help anchor fibers such as fibers 22 shown in FIG. 4 more complex designs of the primary coil 108 may thus be obtained via the heat setting process without reducing the fiber retention capability of the device.

The embolic coils formed according to embodiments of the present invention exhibit advantageous characteristics that make them well suited for use in medical procedures. For example, greater anchorability due to good shape retention and greater fiber retention may be obtained at the same time. Minimization or outright elimination of the high temperature heat treatment process to set and maintain the secondary coil shape increases the manufacturing process throughput, while reduced platinum coil deformation reduces the loss of material due to scrap. The presence of the Nitinol core makes the embolic coil assembly less likely to bind, so that delivery to a selected location within the patient's vascular system is simplified. Since the shape retention/anchorability role is taken up by the shape memory core wire, a smaller profile of the embolic coil is possible. For example, the embodiments according to the invention may provide the anchorability of an 0.035 in. diameter coil in a device having the profile of an 0.010 in. to 0.018 in. coil.

The present invention has been described with reference to specific embodiments associated with an embolic coil having a Nitinol core wire surrounded by a Platinum primary coil. However, other embodiments may be devised that are applicable to other medical devices, without departing from the scope of the invention. In particular, other shape memory metal alloys or polymers may be used in the invention in conjunction with any other suitable biocompatible materials. Accordingly, various modifications and changes may be made to the embodiments without departing from the broadest spirit and scope of the present invention as set forth in the claims that follow. The specification and drawings are accordingly to be regarded in an illustrative rather than restrictive sense.

What is claimed is:

1. An embolic coil comprising:
   an elongated core element formed of a shape memory material and movable between a straightened first configuration and a shape memorized second coiled configuration;
   an elongated outer element which, in the first configuration, is wound around the elongated core element to form a primary coil; and
   a plurality of fibers frictionally gripped by and between adjacent coils of the primary coil.

2. The embolic coil according to claim 1, wherein the shape memory material is formed at an operational temperature of the embolic coil in an austenitic phase.

3. The embolic coil according to claim 1, wherein the memorized shape of the elongated core element is substantially a coil.

4. The embolic coil according to claim 1, wherein the memorized shape of the elongated core element is substantially a three dimensional spiral.

5. The embolic coil according to claim 1, wherein the shape memory material of which the elongated core element is formed includes Nitinol.

6. The embolic coil according to claim 1, wherein the elongated outer element is formed of platinum.

7. The embolic coil according to claim 1, wherein the primary coil shape is a substantially cylindrical coil.

8. The embolic coil according to claim 1, further comprising a plurality of fiber retention grooves formed on the elongated core element.

9. The embolic coil according to claim 1, wherein the elongated outer element comprises a platinum wire co-wound with a wire formed of a shape memory material.

10. A coiled medical device for implantation in a patient comprising:
    a primary coil having a primary coil shape, the primary coil defining a lumen extending therethrough;
    a secondary coil formed of a shape memory material and disposed in the lumen, the secondary coil having a secondary coil memorized shape, wherein, when heated to a temperature above a critical temperature of the shape memory material, the secondary coil causes the primary coil to follow the secondary coil shape; and
    a plurality of fibers gripped by and between adjacent coils of the primary coil and held therebetween by friction.

11. The medical device according to claim 10, wherein the shape memory material includes Nitinol.

12. An embolic coil comprising:
    an elongated core element formed of a shape memory material treated to define a memorized secondary coil shape, the elongated core including a plurality of fiber retention grooves formed in an outer surface thereof;
    an elongated outer element wound around the elongated core element to define a primary coil shape of the embolic coil; and
    a plurality of fibers held within the fiber retention grooves.

13. The embolic coil of claim 12, wherein the fiber retention grooves extend circumferentially about the elongated core element.

14. The embolic coil of claim 12, wherein the fiber retention grooves extend about the elongated core element along a spiral path.

* * * * *